(12) United States Patent
Silver (10) Patent No.: US 7,307,716 B2
(45) Date of Patent: *Dec. 11, 2007

(54) NEAR RE-ENTRANT DENSE PATTERN OPTICAL MULTIPASS CELL

(75) Inventor: Joel A. Silver, Santa Fe, NM (US)

(73) Assignee: Southwest Sciences Incorporated, Santa Fe, NM (US)

( * ) Notice: Subject to any disclaimer, the term of this patent is extended or adjusted under 35 U.S.C. 154(b) by 357 days.

This patent is subject to a terminal disclaimer.

(21) Appl. No.: 10/948,660

(22) Filed: Sep. 22, 2004

(65) Prior Publication Data

US 2006/0158644 A1    Jul. 20, 2006

Related U.S. Application Data

(63) Continuation-in-part of application No. 10/896,608, filed on Jul. 21, 2004.

(51) Int. Cl.
*G01N 1/10* (2006.01)

(52) U.S. Cl. .................................... 356/246; 356/440

(58) Field of Classification Search ............... 356/244, 356/246, 432–440, 301; 250/343, 576
See application file for complete search history.

(56) References Cited

U.S. PATENT DOCUMENTS

| | | | |
|---|---|---|---|
| 4,017,185 A | * | 4/1977 | Chupp .................... 356/326 |
| 4,127,329 A | | 11/1978 | Chang et al. |
| 4,676,639 A | * | 6/1987 | Van Wagenen ............. 356/246 |
| 4,783,789 A | | 11/1988 | Higgins |
| 4,934,816 A | | 6/1990 | Silver et al. |
| 5,291,265 A | | 3/1994 | Kebabian |
| 5,550,375 A | | 8/1996 | Peters et al. |
| 6,087,181 A | | 7/2000 | Cong |
| 6,654,163 B1 | | 11/2003 | Du et al. |
| 7,012,696 B2 | | 3/2006 | Orr et al. |
| 2002/0185603 A1 | | 12/2002 | Daly et al. |
| 2004/0169863 A1 | | 9/2004 | Kawate |

FOREIGN PATENT DOCUMENTS

| | | |
|---|---|---|
| DE | 29 06 536 | 9/1980 |
| DE | 102 16 047 A1 | 10/2003 |
| FR | 2 767 195 | 2/1999 |

OTHER PUBLICATIONS

Abdullin, R. M., et al., "Use of an Integrating Sphere as a Multipass Optical Cell", *Sov. J. Opti. Technol.*, vol. 55, No. 3, (Mar. 1988), 139-141.

(Continued)

*Primary Examiner*—Hoa Q. Pham
(74) *Attorney, Agent, or Firm*—Jeffrey D. Myers; Peacock Myers, P.C.

(57) ABSTRACT

A multiple pass optical cell and method comprising providing a pair of opposed mirrors, one cylindrical and one spherical, introducing light into the cell via an entrance mechanism, and extracting light from the cell via an exit mechanism, wherein the entrance mechanism and exit mechanism are coextensive or non-coextensive.

31 Claims, 8 Drawing Sheets

OTHER PUBLICATIONS

Altmann, J., et al., "Two-Mirror Multipass Absorption Cell", *Appl. Opt.*, vol. 20, No. 6, (Mar. 15, 1981), 995-999.

Chernin, S. M., et al., "Optical Multipass Matrix Systems", *Appl. Opt.*, vol. 30, No. 1, (Jan. 1991),51-58.

Hao, Lu-Uyan, et al., "Cylindrical Mirror Multipass Lissajous System for Laser Photoacoustic Spectroscopy", *Rev. Sci. Instrum.*, vol. 73, No. 5, (May 2002),2079-2085.

Herriott, Donald R., et al., "Folded Optical Delay Lines", *Appl. Opt.*, vol. 4, No. 8, (Aug. 1965), 883-889.

Herriott, Donald R., et al., "Off-Axis Paths in Spherical Mirror Interferometers", *Appl. Opt.* vol. 3, No. 4, (Apr. 1964), 523-526.

McManus, J. B., et al., "Astigmatic Mirror Multipass Absorption Cells for Long-Path-Length Spectroscopy", *Appl. Opt.*, vol. 34, No. 18, (Jun. 20, 1995),3336-3348.

McManus, J. B., et al., "Narrow Optical Interference Fringes for Certain Setup Conditions in Multipass Absorption Cells of the Herriott Type", *Appl. Opt.*, vol. 29, No. 7, (Mar. 1, 1990),898-900.

Salour, Michael M., "Multipass Optical Cavities for Laser Spectroscopy", *Laser Focus*, (Oct. 1977),50-55.

Sigrist, M. W., et al., "Laser Spectroscopic Sensing of Air Pollutants", *Proc. SPIE*, vol. 4063, (2000), 17-25.

Trutna, W. R., et al., "Multiple-Pass Raman Gain Cell", *Appl. Opt.*, vol. 19, No. 2, (Jan. 15, 1980),301-312.

White, John U., "Long Optical Paths of Large Aperture", *J. Opt. Soc. Am.*, vol. 21, (May 1942),285-288.

Yariv, Amnon, "The Propogation of Rays and Spherical Waves", *Introduction to Optical Electronics, Holt, Reinhart, and Winston, Inc., New York, Chap. 2*, (1971),18-29.

Mittenzwey, K-H, et al., "A Portable Absorption-Fluorometer for Detection of Organic Substances in Fluids", *Fresenius J. Anal. Chem.*, vol. 355, (1996), 742-744.

Yao, Lu-Yuan, et al., "Cylindrical Mirror Multipass Lissajous System for Laser Photoacoustic Spectroscopy", *Rev. of Scientific Instruments*, vol. 73, No. 5, (May 2002),2079-2085.

\* cited by examiner

NEAR RE-ENTRANT DENSE PATTERN OPTICAL MULTIPASS CELL

CROSS-REFERENCE TO RELATED APPLICATIONS

This application is a continuation-in-part application of U.S. patent application Ser. No. 10/896,608, entitled "Dense Pattern Optical Multipass Cell", to Joel A. Silver, filed on Jul. 21, 2004, and the specification thereof is incorporated herein by reference.

STATEMENT REGARDING FEDERALLY SPONSORED RESEARCH OR DEVELOPMENT

The U.S. government has a paid-up license in this invention and the right in limited circumstances to require the patent owner to license others on reasonable terms as provided for by the terms of Small Business Research (SBIR) Contracts No. DE-FG02-03ER83779 and NNA04CB22C, awarded by the U.S. Department of Energy and NASA, respectively.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The present invention relates to creation and use of long folded optical paths in a compact structure for use with lasers in making optical measurements or systems.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Multiple pass optical cells with dense spot patterns are very useful for many applications, especially when the cell volume must be minimized relative to the optical path length. Present methods to achieve these dense patterns require very expensive, highly precise astigmatic mirrors and complex alignment procedures to achieve the desired pattern. This invention describes a new, much simpler and less demanding mirror system that can meet all of the requirements and be easily aligned. It comprises of one inexpensive cylindrical mirror and one spherical mirror.

Multiple pass optical cells are used to achieve very long optical path lengths in a small volume and have been extensively used for absorption spectroscopy, (White, J. U., "Long Optical Paths of Large Aperture," *J. Opt. Soc. Am.*, vol. 32, pp 285-288 (May 1942); Altmann, J. R. et al., "Two-mirror multipass absorption cell," *Appl. Opt.*, vol. 20, No. 6, pp 995-999 (15 Mar. 1981) laser delay lines (Herriott, D. R., et al., "Folded Optical Delay Lines," *Appl. Opt.*, vol. 4, No. 8, pp 883-889 (August 1965)), Raman gain cells (Trutna, W. R., et al., "Multiple-pass Raman gain cell," *Appl. Opt.*, vol. 19, No. 2, pp 301-312 (15 Jan. 1980)), interferometers (Herriott, D. H., et al., "Off-Axis Paths in Spherical Mirror Interferometers," *Appl. Opt.*, vol. 3, No. 4, pp 523-526 (April 1964)), photoacoustic spectroscopy (Sigrist M. W., et al., "Laser spectroscopic sensing of air pollutants," *Proc. SPIE*, vol. 4063, pp. 17 (2000)) and other resonators (Yariv, A., "The Propagation of Rays and Spherical Waves," from *Introduction to Optical Electronics*, Holt, Reinhart, and Winston, Inc., New York (1971), Chap. 2, pp 18-29; Salour, M. M., "Multipass optical cavities for laser spectroscopy," *Laser Focus*, 50-55 (October 1977)).

These cells have taken the form of White cells (White, J. U., "Long Optical Paths of Large Aperture," *J. Opt. Soc. Am.*, vol. 32, pp 285-288 (May 1942)) and its variants (Chernin, S. M. and Barskaya. E. G., "Optical multipass matrix systems," *Appl. Opt.*, vol. 30, No. 1, pp 51-58 (January 1991)), integrating spheres (Abdullin, R. M. et al., "Use of an integrating sphere as a multiple pass optical cell," *Sov. J. Opt. Technol.*, vol. 55, No. 3, pp 139-141 (March 1988)), and stable resonator cavities (Yariv, A., "The Propagation of Rays and Spherical Waves," from *Introduction to Optical Electronics*, Holt, Reinhart, and Winston, Inc., New York (1971)).

The stable resonator is typified by the design of Herriott (Herriott, D. H., et al., "Off-Axis Paths in Spherical Mirror Interferometers," *Appl. Opt.*, vol. 3, No. 4, pp 523-526 (April 1964)). The simplest such Herriott cell consists of two spherical mirrors of equal focal lengths separated by a distance d less than or equal to four times the focal lengths f of the mirrors. This corresponds to stable resonator conditions. A collimated or focused laser beam is injected through the center of a hole in one of the mirrors, typically an off-axis location near the mirror edge. The beam is periodically reflected and refocused between these mirrors and then exits through the center of the input hole (corresponding exactly to the entry position of the input beam, defining the re-entrant condition) after a designated number of passes N, in a direction (slope) that is different from the entry slope. As a result, the total optical path traversed in the cell is approximately N×d. The pattern of reflected spots observed on the mirrors in these cells forms an ellipse. Re-entrant conditions for spherical mirror Herriott cells are restricted by certain predetermined ratios of the mirror separation d to the focal length f and the location and slope of the input beam. For any re-entrant number of passes N, all allowed solutions are characterized by a single integer M. Excellent descriptions for the design, setup and use of these cells are given by Altmann (Altmann, J. R., et al., "Two-mirror multipass absorption cell," *Appl. Opt.*, vol. 20, No. 6, pp 995-999 (15 Mar. 1981) and McManus (McManus, J. B., et al., "Narrow optical interference fringes for certain setup conditions in multipass absorption cells of the Herriott type," *Appl. Opt.*, vol. 29, No. 7, pp 898-900 (1 Mar. 1990)).

When the cell volume must be minimized relative to the optical path length or where a very long optical path (>50 m) or very small footprint is desired, it is useful to increase the density of passes per unit volume of cell. The conventional spherical mirror Herriott cell is limited by the number of spots one can fit along the path of the ellipse without the spot adjacent to the output hole being clipped by or exiting that hole at a pass number less than N. This approximately restricts the total number of passes to the circumference of the ellipse divided by the hole diameter, which in turn is limited by the laser beam diameter. For a 25-mm radius mirror with a relatively small 3-mm diameter input hole located 20 mm from the center of the mirror, a maximum of about $(2\times\pi\times20)/3=40$ spots, or 80 passes is possible at best. Generally the hole is made larger to prevent any clipping of the laser input beam that might lead to undesirable interference fringes, and typical spherical Herriott cells employ less than 60 passes.

Herriott (Herriott, D. R. and Schulte, H. J., "Folded Optical Delay Lines," *Appl. Opt.*, vol. 4, No. 8, pp 883-889 (Aug. 1965)) demonstrated that the use of a pair of astigmatic mirrors could greatly increase the spot density, and hence optical path length, in the cell. Each mirror has different finite focal lengths ($f_x$ and $f_y$) along orthogonal x and y axes, and the mirrors are aligned with the same focal lengths parallel to one another. The resulting spots of each reflection on the mirrors create precessions of ellipses to form Lissajous patterns. Since these patterns are distributed about the entire face of each mirror, many more spots can be accommodated as compared to a cell with spherical mirrors. Herriott defines the method of creating the astigmatic mirror as distortion of a spherical mirror, either in manufacture or in use, by squeezing a spherical mirror in its mount. He states that the amount of astigmatism required is very small and amounts to only a few wavelengths. McManus (McManus, et al., "Astigmatic mirror multipass absorption cells for Ion-path-length spectroscopy," *Appl. Opt.*, vol. 34, No. 18, pp 3336-3348 (20 Jun. 1995)) outlines the theory and behavior of this astigmatic Herriott cell and shows that the density of passes can be increased by factors of three or more over spherical mirror cells. For these astigmatic mirror cells, light is injected through a hole in the center of the input mirror. Allowed solutions for re-entrant configurations are characterized by a pair of integer indices $M_x$ and $M_y$, since there are now two focal lengths present along orthogonal axes.

The drawback of this design is that the constraints to achieve useful operation are very severe. First of all, both $M_x$ and $M_y$ must simultaneously be re-entrant, so that for a desired N and variable distance d, the focal lengths $f_x$ and $f_y$, must be specified to a tolerance of 1 part in $10^4$. Since mirrors can rarely be manufactured to such tolerances, this cell as originally proposed is impractical for routine use. However, Kebabian (U.S. Pat. No. 5,291,265 (1994)) devised a method to make the astigmatic cell usable. Starting with the astigmatic Herriott setup with the same mirror axes aligned, he then rotates one mirror relative to the other around the z-axis (FIG. 2), thereby mixing the (previously independent) x and y components of the beam co-ordinates. A moderate rotation of ~5-20 degrees and a small compensating adjustment of the mirror separation distance can accommodate the imprecision in the manufacturing of the mirror focal lengths. However, this approach is still difficult to achieve in practice and requires complex calculations and skill to get to the desired pattern. Furthermore, the astigmatic mirrors must still be custom made and cost many thousands of dollars for a single pair.

Recently, Hao (Hao, L.-Y., et. al., "Cylindrical mirror multipass Lissajous system for laser photoacoustic spectroscopy," *Rev. Sci. Instrum.*, vol. 73, No. 5, pp. 2079-2085 (May 2002)) described another way to generate dense Lissajous patterns using a pair of cylindrical mirrors, each having a different focal length, and where the principal axes of the mirrors are always orthogonal to one another. In essence, this creates a pair of mirrors whose x-axis contains one curved surface (on mirror A) of focal length $f_x$ and one flat mirror surface (on mirror B), and in the y-axis contains one flat mirror surface (on mirror A) and one curved surface of focal length $f_y$ (on mirror B), where $f_x \neq f_y$. Formulas to predict the spot patterns on each mirror are provided. The advantage to this system is that the dense Lissajous patterns can be formed from a pair of inexpensive mirrors, in contrast to the requirement for custom astigmatic mirrors (we note that for a practical commercial multipass cell, one cannot rely on simply squeezing spherical mirrors to achieve a reliable long term, stable set of focal lengths. Thus diamond turned custom astigmatic mirrors must be made). The drawback of this mismatched focal length pair of cylindrical mirrors is that, similar to the astigmatic Herriott cell, for a given pair of focal lengths, there is only one allowed re-entrant solution value of N permitted. Of course, for photoacoustic measurements as intended by Hao, where any exiting light is not detected, the light does not necessarily have to be re-entrant and many values of mirror separation which are not re-entrant, but do generate many passes, are useful.

Silver, in U.S. patent application Ser. No. 10/896,608, parent to the present application, recently introduced a method for achieving dense patterns using a pair of nominally matched cylindrical mirrors whereby the desired patterns can readily and reliably be set using inexpensive mirrors. A key feature of this system is that nearly any reasonable number of passes can be achieved using a single set of mirrors, in contrast to the orthogonal mismatched cylindrical pair of Hao or the astigmatic mirrors of Kebabian. The desired number of passes and overall optical path are set by rotating the cylindrical axes relative to one another at a predetermined mirror separation.

The present invention describes a very simple, low cost, high density, multipass optical cell, where no rotation of the mirrors is needed (in fact, with a spherical-cylindrical mirror pair, no rotation axis can be defined because the spherical mirror is fully symmetric). The key to this invention is to use near, but not exact re-entrant conditions as are common to all of the above-referenced methods. Contrary to the teachings of all multipass mirror papers and patents, exact re-entry is not a necessary criterion for practical use, but does simplify use in most cases. However, with the spherical-cylindrical mirror pair, there are very few or no exact re-entrant solutions (depending on the focal lengths of the mirrors) but only a limited, but useful, number of nearly re-entrant solutions exist. Thus it becomes a relatively easy task to identify good near re-entrant solutions and to align any given mirror system to achieve these solutions. As long as this mirror system is a stable resonator, then the desired number of passes can be achieved simply by setting d to the predicted value based on the mirror focal lengths. When the laser beam enters through the center of one mirror, a dense pattern of spots forms and the position of the beam as it exits this hole is readily predicted.

Unlike all other dense cell methods, this invention relies neither on the absolute manufactured focal lengths or mirror twist angles, but only on the relative mirror separation ratio d/f.

BRIEF SUMMARY OF THE INVENTION

The present invention is of a multiple pass optical cell and method comprising: providing a pair of opposed mirrors, one cylindrical and one spherical; introducing light into the cell via an entrance mechanism; and extracting light from the cell via an exit mechanism; and wherein the entrance mechanism and exit mechanism are coextensive or non-coextensive. In the preferred embodiment, the invention rotates at least the cylindrical mirror with respect to the long axis of the cell, mirror separation is adjusted, and a plurality of number of passes of light between the two mirrors exists for light entering the entrance mechanism and exiting the exit mechanism for any given combination of mirror separation distance and rotation position of the cylindrical mirror with respect to a long axis of the cell. Alternatively, no rotation can be performed, and only mirror separation adjustment is performed, which adequately adjusts to account for manufacturing tolerances as to mirror focal lengths. Preferably the mirrors are initially aligned by using a fully reentrant test condition.

The present invention is also of a multiple pass optical cell and method comprising: providing a pair of opposed mirrors; introducing light into the cell via an entrance mechanism; and extracting light from the cell via an exit mechanism; and wherein the entrance mechanism and exit mechanism are coextensive or non-coextensive; and wherein a plurality of number of passes of light between the two mirrors exists for light entering the entrance mechanism and exiting the exit mechanism, but wherein a pattern of spots on the mirrors established by the plurality of passes of light is non-reentrant. The preferred embodiment is as described in the preceding paragraph.

A primary object of the present invention is to generate a very long optical path in a compact cell.

Another object of the invention is to keep the cost of this cell low so as to permit widespread commercial availability and feasibility.

Another object of this invention is to make a dense multipass cell where one set of mirrors permits a wide range of configurations having many different numbers of allowed passes.

Another object of this invention is to make alignment of the desired number of optical passes easier, quicker and more reliable to accomplish.

A primary advantage of the present invention is that is can be used in a wide variety of optical applications and can be constructed at significantly lower cost as compared with other dense pattern optical designs.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

The present invention describes a simple, low cost and more easily aligned high density multipass optical cell, where many different paths can be achieved with one set of mirrors. The key to this invention is the use of one cylindrical mirror and one spherical mirror and includes the use of near re-entrant conditions, so as to remove the severe restrictions imposed in other dense pattern systems with astigmatic mirrors or crossed cylindrical mirror pairs. Since the present invention is fully symmetric to rotation of one mirror relative to the other, there is no need to consider relative twisting of the mirrors along their central axes. It is also insensitive to any manufacturing tolerance errors in the focal lengths of the mirrors.

For purposes of the specification and claims, a "cylindrical mirror" is one for which one radius of $r_x$ and $r_y$ is substantially infinite, the non-infinite axis being known as the "curved axis". This is in contradistinction to a "flat mirror", for which both radii are substantially infinite, and a "spherical mirror" for which both radii are non-infinite and substantially equal. An "astigmatic mirror" is a mirror for which both radii are non-infinite but not equal, usually deviating slightly from one another by design. "Near re-entrant" is defined as having the light beam exit the input hole at an x, y position close to, but not exactly equal to, the input beam position $x_0$, $y_0$.

The present invention involves injecting the laser beam through a hole in the center of either one of the mirrors and adjusting the mirror separation distance until the light exits this hole after a desired number of passes within the cell. Without complex alignment procedures, one can readily generate known dense patterns and much longer optical path lengths than with a simple Herriott cell, and with much less cost or complication than with astigmatic cells. Specific near re-entrant conditions have been identified and are easily set by various combinations of input beam slope and mirror separation.

Figure 1:
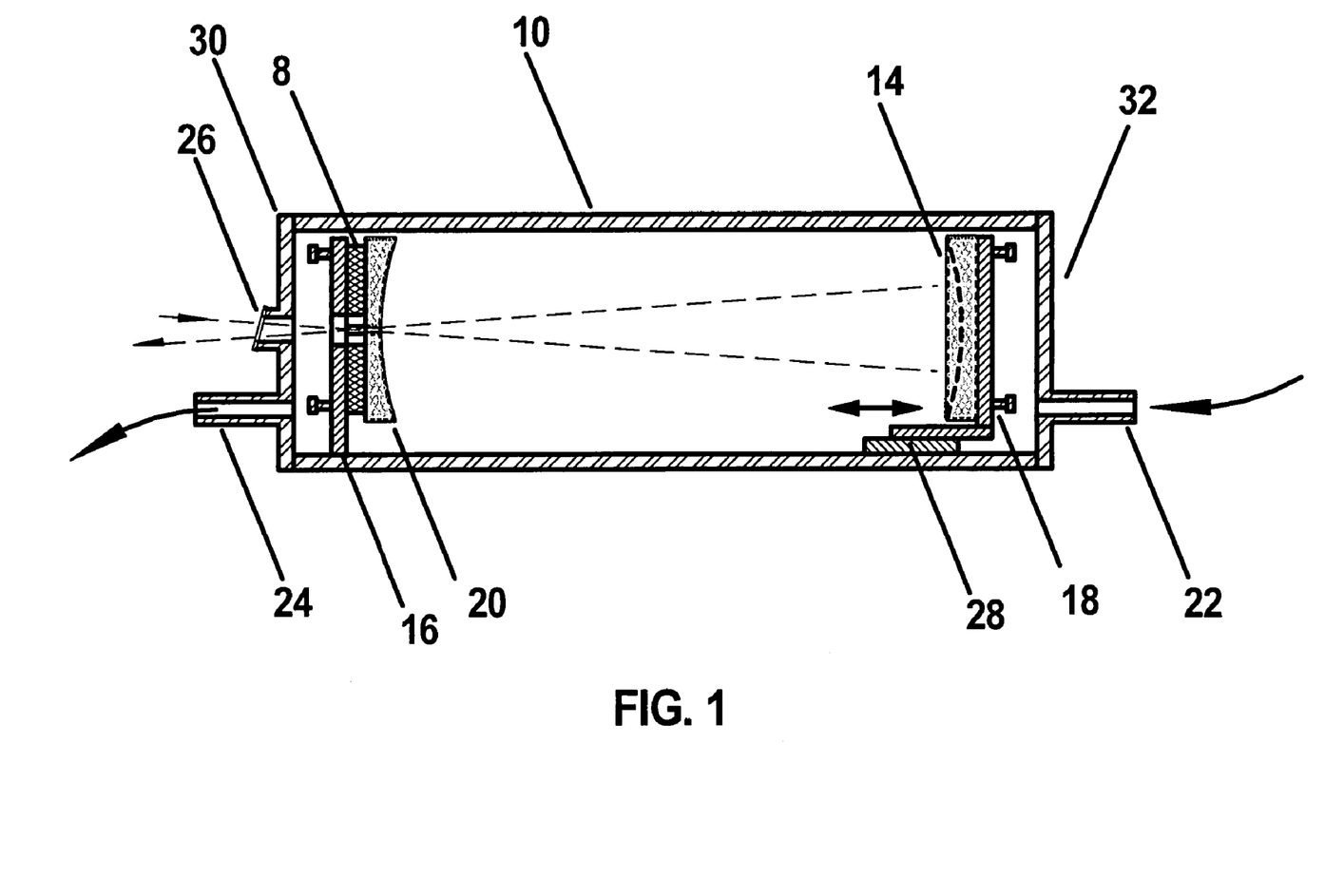
FIG. 1 is a drawing of the preferred embodiment of the present invention.

FIG. 1 is a drawing of the preferred embodiment for the present invention. The cylindrical mirror 20 and spherical mirror 14 are attached to adjustable-tilt mirrors mounts 16 and 18, respectively, which are attached to an open frame or closed cell 10 separated by distance d. In this example, one of the mirror mounts is attached to a means 28 to permit variable adjustment of the mirror separation. A light source or laser is pointed into the cell at the appropriate direction (slope) and a detector mounted outside the cell collects the light after transmission through the multiple pass optics. In the case of a closed cell, the gas is input at one end 22 and pumped out through a second port 24 at the other end. In this case, sealed end flanges 32 and 30 are attached to the cell wall. A window 26 is used to permit the light to enter and exit the sealed cell so that no ambient gas can interfere with the gas sample inside the cell. An optional rotation stage 8 allows the user to rotate the axis of the cylindrical mirror relative to the cell axis.

This description begins with a discussion of the prior art spherical Herriott cell theory and then briefly describes the prior art astigmatic cell design and restrictions to provide a basis for the new cylindrical-spherical cell invention.

Figure 2:
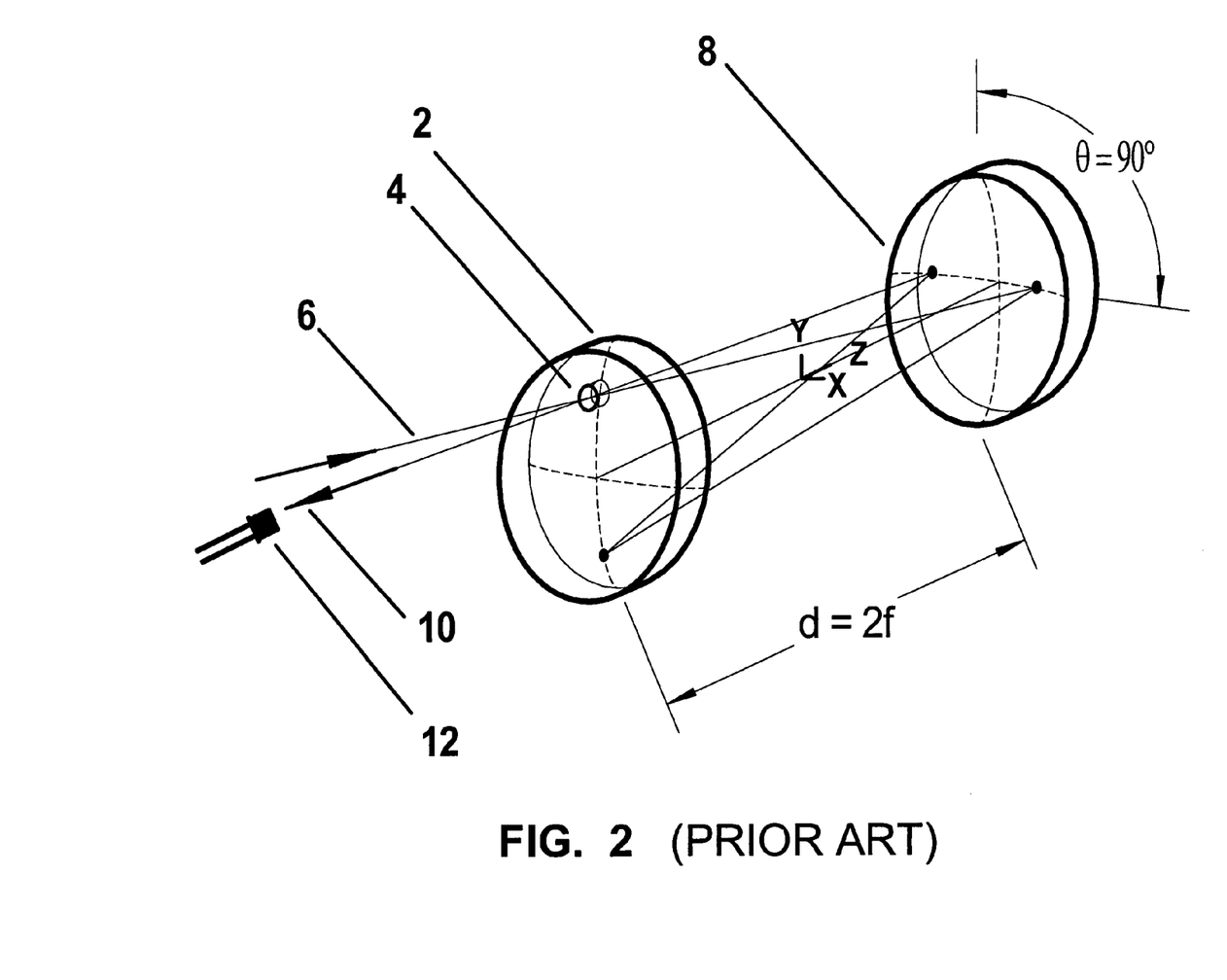
FIG. 2 is a drawing of a conventional spherical mirror Herriott cell.
Figure 3:
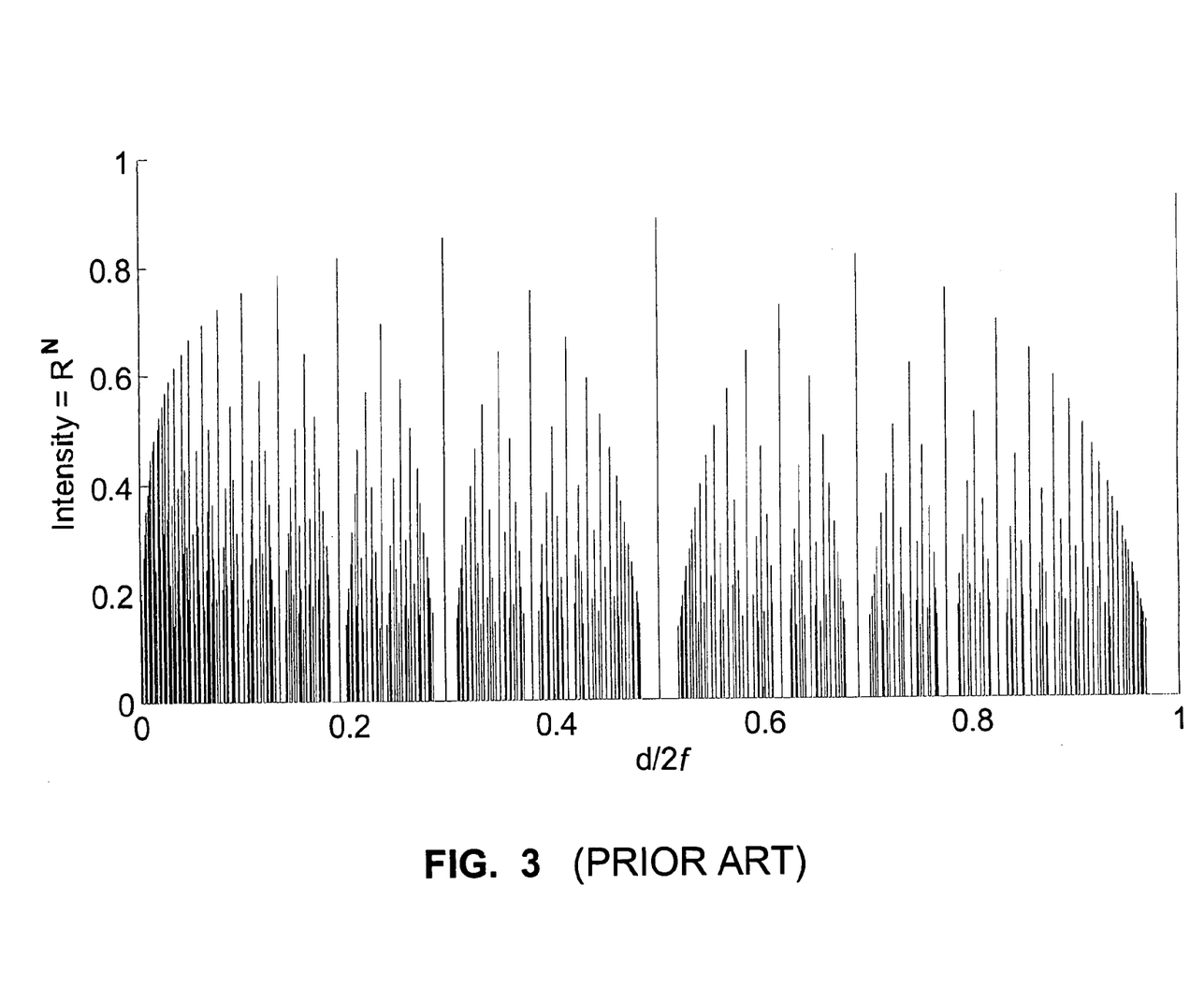
FIG. 3 is a plot of the patterns of allowed re-entrant passes for a spherical mirror Herriott cell as a function of dimensionless mirror separation d/2f. The transmitted intensity is equal to $R^N$, where R is the reflectivity of the mirrors (0.98 here) and N the total number of passes through the cell.

As generally set up (FIG. 2), the normal Herriott cell comprises one spherical mirror ("front") 2 of focal length f with an off-axis entrance hole 4 (at co-ordinates $x_0$ and $y_0$) through which the laser beam 6 is injected with slopes $x_0'$ and $y_0'$ and pointed at a second spherical mirror 8 ("rear"), also of focal length f. This beam is then periodically reflected and refocused such that the beam eventually exits exactly through the center of the input hole 4 (re-entrant condition) but in the opposite direction (slope) of the input beam so as to make possible the placement of a detector 12 without obstructing the input beam. The conditions for re-entry and the number of passes in the cell (even integer N) are governed by the focal lengths of the mirrors f, their separation d and the initial slopes of the input beam ($x_0'$ $y_0'$) relative to the ratio of d/f. The total optical path within the cell is approximately d×N. The patterns of spots on the mirrors trace out an ellipse, where the co-ordinates of the spots of the $i^{th}$ pass are:

$$x_i = x_0 \cos(i\theta) + \sqrt{\frac{d}{4f-d}}(x_0 + 2fx_0')\sin(i\theta), \quad (1)$$

with a corresponding equation for y. Thus $x_i$ is the projection of the maximum position ($X_{max}$) in the spot pattern. The $x_i$ position changes on each pass with an incremental increase of integer i in the angle θ. For the off-axis injection of the laser beam as shown in FIG. 2, the light will exit the cell exactly through the center of the input hole at $x_0$ and $y_0$ after an integral number of 2π multiples of θ, so that:

$\theta_R = 2\pi M/N$ and $$d = 2f(1-\cos\theta_R), \quad (2)$$

where the number of complete orbits of spots before exiting is denoted by the integer index M; $\theta_R$ is the angular projection advance angle for each sequential pass. This configuration defines an allowed re-entrant condition. Thus after N passes, the spot pattern has rotated a multiple of 2π in both x and y co-ordinates, and exits through the input hole. While many possible solutions for N and M exist for any given set of input conditions, the generally used initial conditions (with the off-axis input hole defined as $x_0=0$, $y_0=1$) is to align the first pass at $x_1=1$, $y_1=0$ (i.e., input slopes corresponding to $x_0'=1$, $y_0'=-1$ in reduced units of d/2f). This condition generates a circle with N=4 at d=2f. This is illustrated in FIG. 2. Under these conditions, all patterns can be characterized by:

$$N = 4M \pm K, \quad (3)$$

where K is an even integer, and positive K correspond to solutions of d<2f and negative K to solutions for d>2f (up to a maximum allowed separation of 4f). In general, -K solutions are not as useful since the beam patterns trend toward being much larger in size than the input hole position as the mirror separation increases beyond 2f. While many different (M, N) pairs can generate the same fraction (angular advance θ) in Eqn. 2, only the set with the lowest N is allowed. All other sets cannot be achieved since the pattern will exit at a pass number less than N. For example, M=2, N=10 gives a fraction of ⅕ and θ=0.4π. Since M=4 and N=20 also gives a fraction of ⅕, this 20-pass configuration can't be achieved because the beam would exit after the tenth pass. As further elaborated by McManus, these rules can be formalized by computing modulo orders of the corresponding K values for any N (McManus, J. B. and Kebabian, P. L., "Narrow optical interference fringes for certain setup conditions in multipass absorption cells of the Herriott type," *Appl. Opt.*, vol. 29, No. 7, pp 898-900 (1 Mar. 1990)). FIG. 3 illustrates the pattern of allowed solutions for the spherical Herriott cell as a function of the ratio d/2f. The transmitted intensity is equal to $R^N$, where R is the reflectivity of the mirrors (0.98 here) and N the total number of passes through the cell. For d>2f, the pattern is just a mirror image reflected about d=2f. The patterns of allowed passes correspond to various families of {N, M, K}.

The useful properties of the spherical Herriott cell are that virtually any desired optical path length and number of passes can be achieved by simply adjusting the mirror separation distance. The output spot position is fixed regardless of the spot pattern or number of passes, and this output position is invariant to slight tilt or misalignment of the mirrors. Thus once the initial beam is aligned and the detector located, the number of passes and path length are readily adjusted by simply moving the position of the rear mirror along the axis.

High Density Cells

In order to achieve a higher density of spots, which leads to longer paths lengths for the same sized cell, Herriott developed a multipass optical cell using a pair of astigmatic mirrors (Herriott, D. R. and Schulte, H. J., "Folded Optical Delay Lines," *Appl. Opt.*, vol. 4, No. 8, pp 883-889 (August 1965)). Each mirror has a different finite focal length along its orthogonal x and y axes, $f_x$ and $f_y$. Thus unlike the spherical cell, the astigmatic cell x and y co-ordinates have separate, independent solutions. With the input hole now in the center of the mirror, the x and y co-ordinates for the $i^{th}$ spot are defined by:

$x_i = X_{max}\sin(i\theta_x)$, $y_i = Y_{max}\sin(i\theta_y)$, $\theta_x = \cos^{-1}(1-d/2f_x)$, and $$\theta_y = \cos^{-1}(1-d/2f_y), \quad (4)$$

where $X_{max}$ and $Y_{max}$ are the maximum positions of x and y in the spot pattern. The re-entrant solutions for $M_x$ and $M_y$ are slightly different than in Eqn. (2), $\theta_{xR} = \pi M_x/N$, and $$\theta_{yR} = \pi M_y/N, \quad (5)$$

because the beam can exit after only π radians, rather than a full 2π when the input hole is at the edge of the pattern. M here can be viewed as the number of half-orbits of spots before each co-ordinate exits. As a result, the allowed indices are now defined here by:

$$N = 2M_x + K_x = 2M_y + K_y. \qquad (6)$$

Thus, to achieve re-entrant conditions, two simultaneous equations must be solved for a desired set of [N, $M_x$, $M_y$]. This results in specific design values for d, $f_x$ and $f_y$, making the system much less flexible for being able to select N with a particular set of mirrors. This is in contrast to the normal spherical Herriott cell where the ratio of d/f can be adjusted to give a range of thetas, and thus a series of many differing re-entrant spot patterns for a given mirror pair. Since both half and full orbits of the spot patterns can be re-entrant, the beam can exit into any quadrant of x-y space. Optimal solutions can be found where the beam exits in a plane opposite the input beam onto a unique, fixed position, where patterns minimize spots near the input hole and where common factors (lower order exits at passes<N) are avoided. These solutions require that N/2 be an odd integer and $M_x$ and $M_y$ be even integers.

In order to achieve a re-entrant design, manufacturing criteria on the precision for d, $f_x$ and $f_y$ are so severe that a commercially produced cell is almost impossible to make reliably and repeatedly. The focal lengths must be precise to better than 1 part in $10^4$. Kebabian (U.S. Pat. No. 5,291,265 (1994)) devised a method to make the astigmatic cell usable by rotating the axis of one astigmatic mirror relative to the other and thereby mixing the (previously independent) x and y components of the beam co-ordinates. A moderate rotation of ~5-20 degrees and a small compensating adjustment of the mirror separation distance can accommodate the imprecision in the manufacturing of the mirror focal lengths. However, this approach is still difficult to achieve in practice and requires complex calculations and skill to get to the desired pattern. Furthermore, the astigmatic mirrors must be custom made and cost many thousands of dollars for a single pair.

Numerical Determination of Spot Patterns

In all of these Herriott-style systems, the precise patterns of spot locations can be computed either directly from matrix multiplication methods or from analytic solutions of the relevant ray tracing equations derived from these matrices.

Using ray matrix theory as outlined by Yariv (Yariv, A., "The Propagation of Rays and Spherical Waves," from Introduction to Optical Electronics, Holt, Reinhart, and Winston, Inc., New York (1971), Chap. 2, pp 18-29), the propagation of light rays through an optical system is readily understood. Given the $x_0$ and $y_0$ components and respective slopes $x_0'$ and $y_0'$ of the incident ray, the positions and slopes after each action (translation, reflection, etc.) are:

$$r_{i+1} = \begin{bmatrix} x_{i+1} \\ x'_{i+1} \\ y_{i+1} \\ y'_{i+1} \end{bmatrix} = M \cdot r_i = [4 \times 4] \begin{bmatrix} x_i \\ x'_i \\ y_i \\ y'_i \end{bmatrix}, \qquad (7)$$

where the $(i+1)^{th}$ vector r is related to the previous pass i by a square matrix M that represents coefficients that perform the specified optical operation. For the specific case of two mirrors, we can find the position and slopes of the ray after one round-trip of the cell, denoted by index n, as the product of $R_1 \cdot D \cdot R_2 \cdot D \equiv C$, where R is a reflection matrix, D a translation matrix and the subscripts 1 and 2 correspond to each of the two mirrors. For n round trips, then we can express $r_n = C^n \cdot r_0$.

If the x and y components are uncoupled, then we can use separate 2×2 matrices for each x and y component. Thus the four elements of the solution C can be expressed as:

$$C = \begin{bmatrix} A & B \\ C & D \end{bmatrix}, \qquad (8)$$

The relevant matrices for translation and reflection, where f is the focal length (radius of curvature/2) along the specified component axis and d the separation, are:

$$D = \begin{bmatrix} 1 & d \\ 0 & 1 \end{bmatrix} \text{ and } R = \begin{bmatrix} 1 & 0 \\ -1/f & 1 \end{bmatrix}. \qquad (9)$$

From the equations above, C can be computed using matrix multiplication and the resulting elements of C used to derive a recursive solution for each 2×2 operation for x (or similarly y) as:

$$x_{n+2} - 2bx_{n+1} + \gamma x_n = 0, \qquad (10)$$

where $b = \frac{1}{2}(A + D)$ and $\gamma = AD - BC = 1$.

It can also be shown that b=cos(2θ), where 2θ is twice the advance angle defined in Eqn. 1, since this formulation is describing a round-trip of two sequential passes. The stability criterion for θ to be real also creates the restriction |b|≦1. The angle theta is the centroid of revolution of the x or y component.

For the prior art astigmatic Herriott cell (without rotation of the mirrors), there are different solutions for $\theta_x$ and $\theta_y$, so that re-entrant solutions must satisfy two simultaneous equations.

If the principal axis of a non-spherical mirror is not aligned with x or y, but twisted by an angle δ, as suggested by Kebabian, then a 4×4 matrix must be used to include cross-terms (coupling of x and y) and the rotation matrix for this situation is defined by $R' = T(-\delta) \cdot R \cdot T(\delta)$, $$T(\delta) = \begin{bmatrix} \cos\delta & 0 & \sin\delta & 0 \\ 0 & \cos\delta & 0 & \sin\delta \\ -\sin\delta & 0 & \cos\delta & 0 \\ 0 & -\sin\delta & 0 & \cos\delta \end{bmatrix}. \qquad (11)$$

This rotated reflection matrix and its corresponding 4×4 translation matrix must be used when either mirror is rotated away from an orthogonal axis. Note that this matrix approach is general in nature and can be used for any two-mirror system.

For the present cylindrical-spherical cell, there is no possible relative rotation of mirror axes, so all analyses use the simpler 2×2 matrix formulas.

Analytic Formulation

From the formulations presented above, generalized analytic solutions similar to Eqn. 10 can be derived for any mirror system, where the positions of each spot for the $n^{th}$ round-trip are given by a recursion formula. Unfortunately, for those systems requiring relative rotations of mirrors (coupling of x and y axes), the solutions are very complicated algebraic expressions and the matrix formulation for these systems is preferred.

Detailed Solutions for a Cylindrical-Spherical Mirror System

Turning now to the present invention, define the cylindrical-spherical mirror cell (FIG. 4) as having one cylindrical mirror 2 with its focal length $f_{cyl}$ of its curved axis arbitrarily defined in the y-z plane and one spherical mirror 4 with focal length $f_{sph}$. In this case the input mirror is cylindrical and the rear (folding) mirror is spherical, but this configuration could just as well be reversed. The input hole 6 is located in the center of mirror 2.

Figure 4:
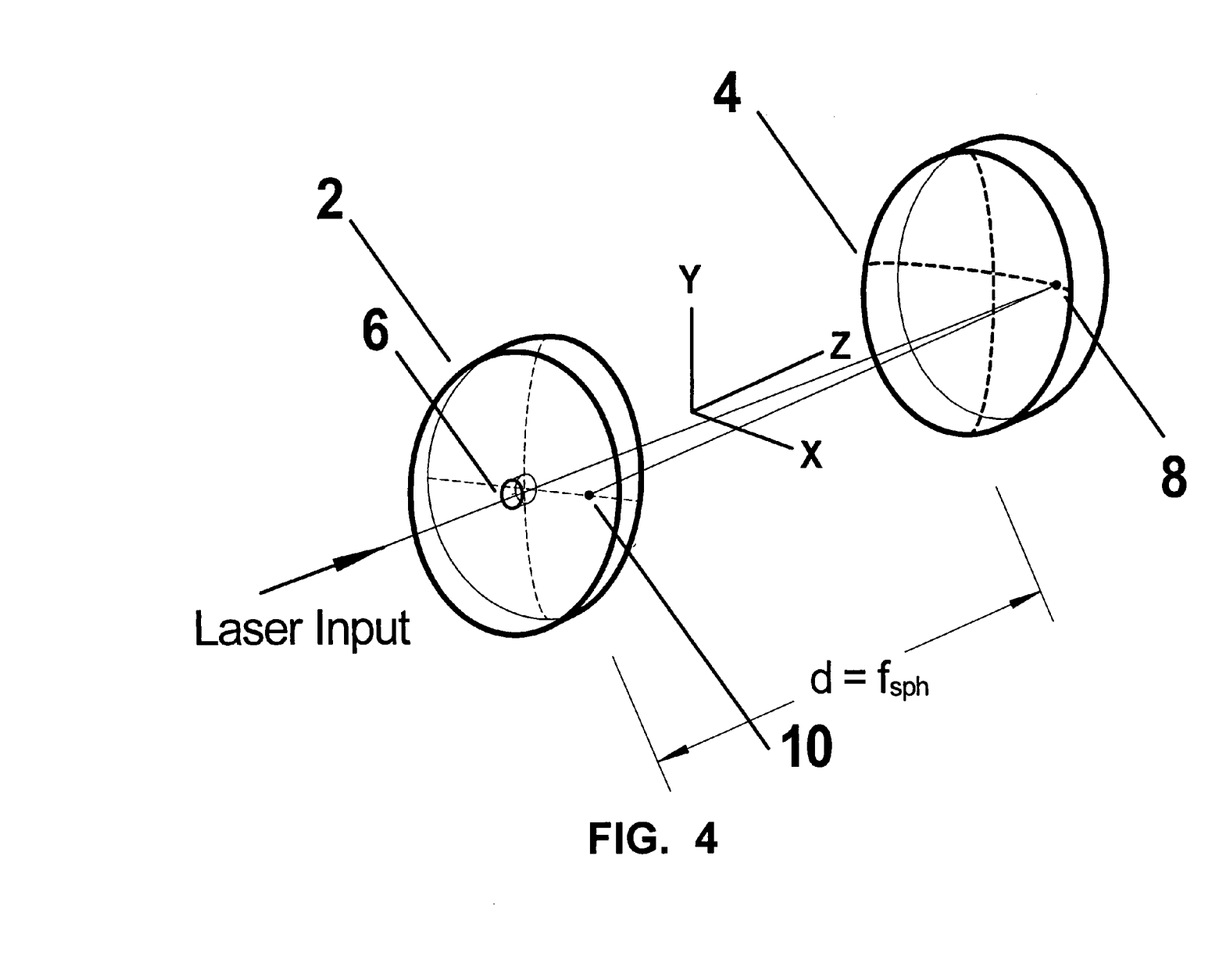
FIG. 4 is a drawing of the cylindrical-spherical mirror cell of the invention having a center on-axis input hole and set for the initial alignment condition of four passes.

This optical system can be simply represented by 2×2 matrices derived from Eqn. 9 where the x-coordinate $R_1$ uses 0 and $R_2$ uses $1/f_{sph}$ for the inverse focal lengths, and the y-coordinate for $R_1$ uses $1/f_{cyl}$ and $R_2$ uses $1/f_{sph}$. Solving for b and y in Eqn. 10, the stability criteria as discussed earlier become:

$$0 \le d \le 2f_{sph}, \quad x\text{-axis} \quad (12)$$

$$0 \le \left(1 - \frac{d}{2f_{sph}}\right)\left(1 - \frac{d}{2f_{cyl}}\right) \le 1, \quad y\text{-axis}$$

where the smaller of the distances for x or y is limiting. Similar to Eqn. 10, the spot locations for the $n^{th}$ round-trip are expressed by a recursion formula $$x_{n+2} - 2\left(1 - \frac{d}{f_s}\right)x_{n+1} + x_n = 0, \quad \text{and} \quad (13)$$

$$y_{n+2} - 2\left(1 - \frac{d}{f_{sph}} - \frac{d}{f_{cyl}} + \frac{d^2}{f_{sph}f_{cyl}}\right)y_{n+1} + y_n = 0.$$

Figure 5:
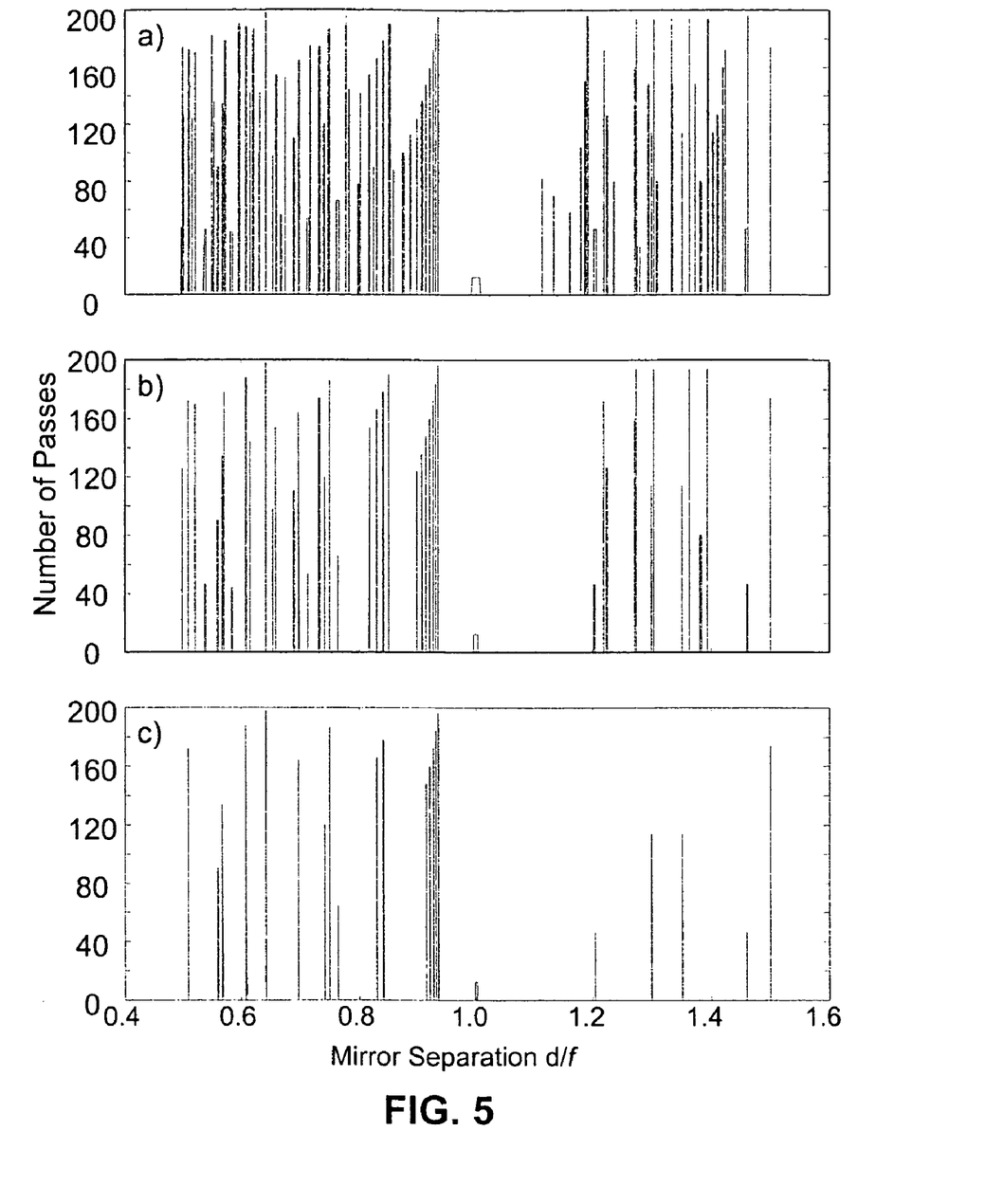
FIG. 5 is a plot of the number of passes which exit the input hole of a cylindrical-spherical mirror cell as a function of dimensionless mirror separation $0.5 \leq d/f \leq 1.5$, with the ratio of input hole diameter to maximum spot pattern size being a) 0.05, b) 0.025 and c) 0.0125. For this calculation, the same focal length is assumed for both mirrors.

For any specified set of mirrors, we can use the matrix or analytic equations to follow the spot positions on the input mirror for each pass (given the input slope and input hole diameter) to determine at which pass number the beam exits the hole as a function of mirror separation distance d. FIG. 5 is a plot of near re-entrant pass number for beams exiting the cell as a function of mirror separation d. In these calculations, the mirror separation is varied from 0.5<d/f<1.5, in steps of 0.008 d/f, where the focal lengths of both mirrors are kept equal for convenience.

If one examines the location of any given spot with pass number N on the input mirror as the mirror separation is smoothly varied, its position maps out a Lissajous pattern that at some point crosses the exit hole. After some additional small distance change it again resumes its trajectory on the mirror surface until its next encounter with the hole. Of course, if one wanted to use this N number of passes, one would simply adjust the distance so that the exiting beam was as closely spaced to the center of the hole as possible (defining the near re-entrant condition). In cases where the spot is exactly centered, this is a true re-entrant condition as described earlier. For any cylindrical-spherical system where both mirrors have the same focal length, there is only one exactly re-entrant solution: This corresponds to 12 passes at d=f. For unequal focal lengths, there is generally no re-entrant solution, although for specific combinations of mirror focal lengths, corresponding re-entrant solutions do exist.

For a large input hole, the beam tends to exit after fewer passes than when the hole is small, since its trajectory is more likely to encounter the bigger hole. A larger input slope causes the overall spot pattern to cover a larger area, thus spreading out the spots. Thus the proper scaling factor is the ratio of the hole size to input slopes. In addition, since the input slopes are generally maximized to make the pattern as large as possible to best fill the mirrors, then the ratio of the input hole diameter to mirror diameter is also a useful scaling parameter. The variation of near re-entrant pass numbers with mirror separation for a few different input diameter-to-maximum pattern size ratios is shown in FIG. 5 (limited to 200 passes maximum). As expected, as the hole gets relatively smaller, the number of solutions (for N<200) decreases.

Figure 6:
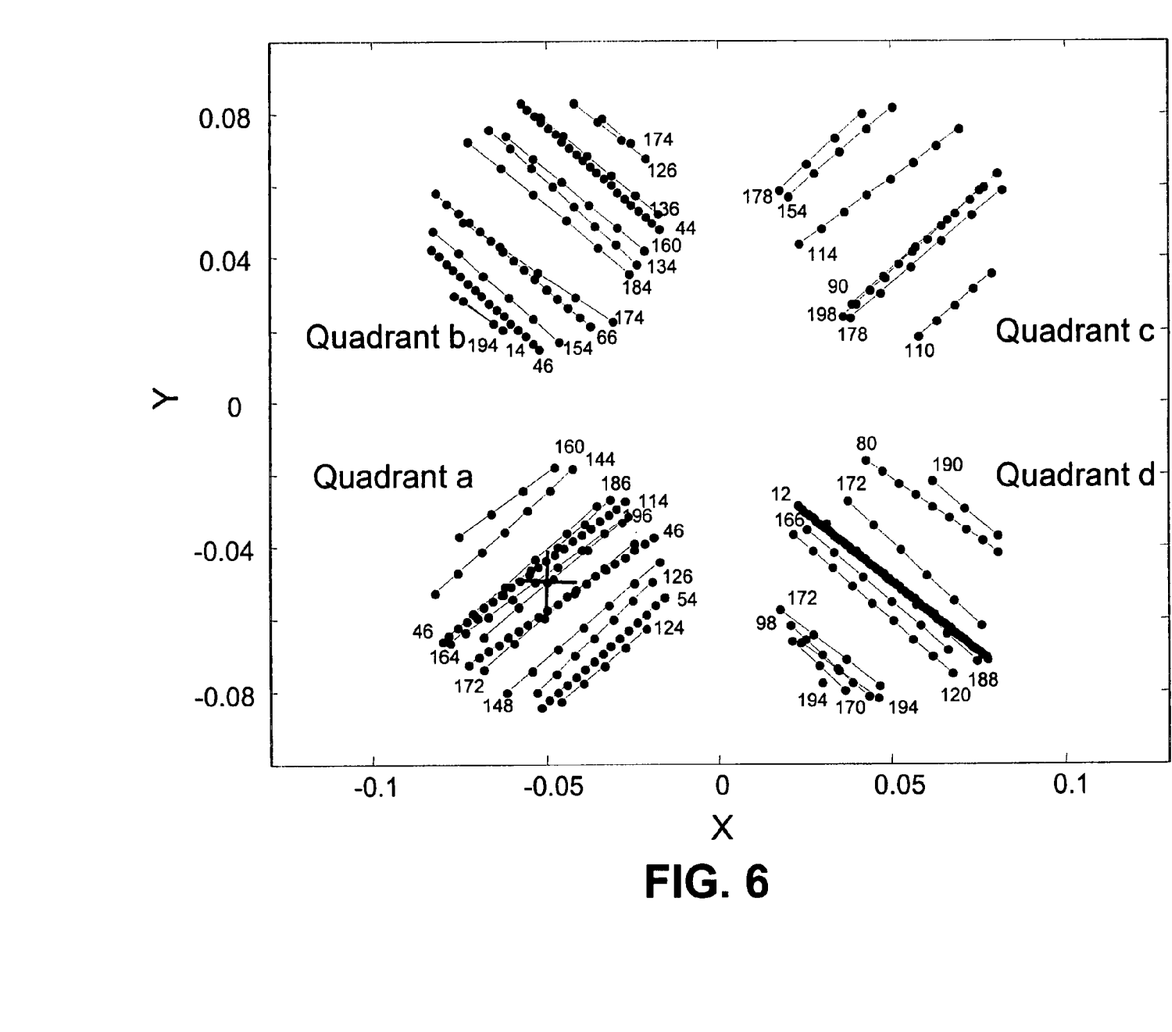
FIG. 6 is a plot of the beam exit locations in the x-y plane just outside the input mirror for case b of FIG. 5, noting the exit pass number and quadrant. The + symbol in the lower left quadrant denotes the location of the input beam in this plane.

The exit slope is also important. Like the fully re-entrant systems, one would like the exiting beam to be physically separated from the input beam so as to permit placement of additional optical components or a photodetector without clipping or blocking the input beam. FIG. 6 is a plot of the beam exit locations (using the case of FIG. 5b) in the x-y plane just outside the input mirror, computed by noting the exit pass number. Over the small region of d where a given Nth spot exits, the spot position moves across the hole as described above, where the circular symbols on each line correspond to individual steps of d/f of 0.008. Note that for lower N the spot trajectory travels more slowly across the hole and for higher N, the symbols are more widely spaced as the velocity of the trajectory increases. The input beam location is noted by the + symbol in quadrant a. The most useful exit conditions are those where the beams are in the quadrant opposite the input beam, although adjacent quadrants can also be used for placing the detector. In any case, any of quadrants b, c, or d has a sufficient number of solutions to be useful for selecting a wide range of N for measurement.

Presently Preferred Embodiment

A commercial 5 cm-square cylindrical mirror with $f_{cyl}$=64.84 mm (Newport Corporation, Model 03SI31512) and a 2-inch diameter spherical mirror with $f_{sph}$=100 mm were assembled on mounts on an optical rail so that the separation could be smoothly varied. As illustrated in FIG. 4, the cylindrical front mirror 2 is aligned so that the radius of curvature is in the y-z plane. For initial alignment steps, the output of a JDS Uniphase He—Ne visible laser (632.8 nm) was injected through a 3/16" dia. hole 6 in the center ($x_0$=0, $y_0$=0) of the front mirror such that at a separation equal to the focal length of the rear spherical mirror 4 (d=$f_{sph}$=100 mm), the first spot 8 strikes the rear spherical mirror at $x_1$=20 mm, $y_1$=0 mm (with a slope arbitrarily defined in reduced units as $x_0'$=1, $y_0'$=0). The reflectivity of these mirrors at 632 nm is approximately 0.975. The intensity of the output beam from the cell is monitored by a silicon photodiode (UDT Model Number 2DI). Since the source of the first spot on the spherical mirror originates at a distance equal to its focal length, the reflected beam is then collimated (parallel) to the cell axis and strikes mirror 2 (spot number 2) at position 10 that also has co-ordinates $x_2$=20 mm, $y_2$=0. Since the cylindrical mirror is flat along the x-axis at y=0, the cylindrical mirror here acts as a flat mirror and the beam retraces its initial path back to spot 1 (pass number 3) and out the center of input hole (pass four) exactly aligned along the path of the input beam. As shown in FIG. 4, this four pass (fully re-entrant) alignment condition is very simple and permits the initial proper settings of tilt adjustments and separation of the mirrors to make them parallel and define the separation axis.

Figure 7:
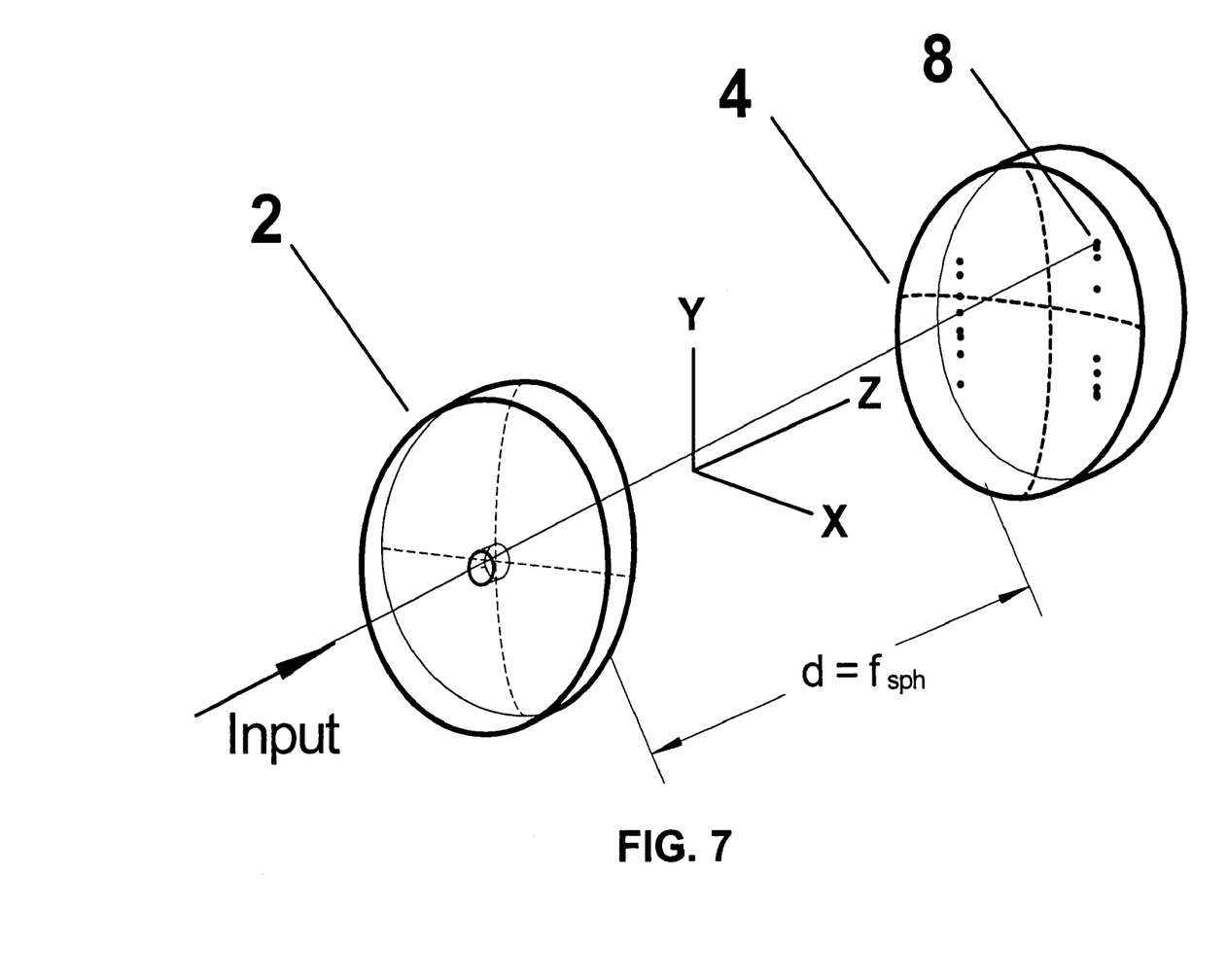
FIG. 7 is a drawing of the cylindrical-spherical mirror cell of the invention having a center on-axis input hole and set for an initial alignment condition having two rows of spots.

If the input slopes are now adjusted to $x_0'=0.7071$, $y_0'=0.7071$ ($x_1=y_1=14.14$ mm), then pattern of spots appears as illustrated in FIG. 7. We note that although this mirror system is insensitive to rotation of one mirror relative to another (unlike any of the other dense pattern multiple pass cell methods), rotation of the entire cell (or equivalently, rotation of the cylindrical mirror only since the spherical mirror is fully symmetric about the rotation axis) is identical to changing the input slopes as long as the radial distance from the center of mirror 4 to the spot 8 is unchanged. For this reason, the optional rotation stage 8 in FIG. 1 is included. As a result, this new set of slopes results in patterns fully equivalent to those observed if instead the cylindrical mirror axis had been rotated by 45 degrees relative to the initial input slopes. In this case, a near re-entrant dense pattern comprising two lines of spots is observed on the rear mirror 4, for a total of 36 passes before exiting the cell.

Figure 8:
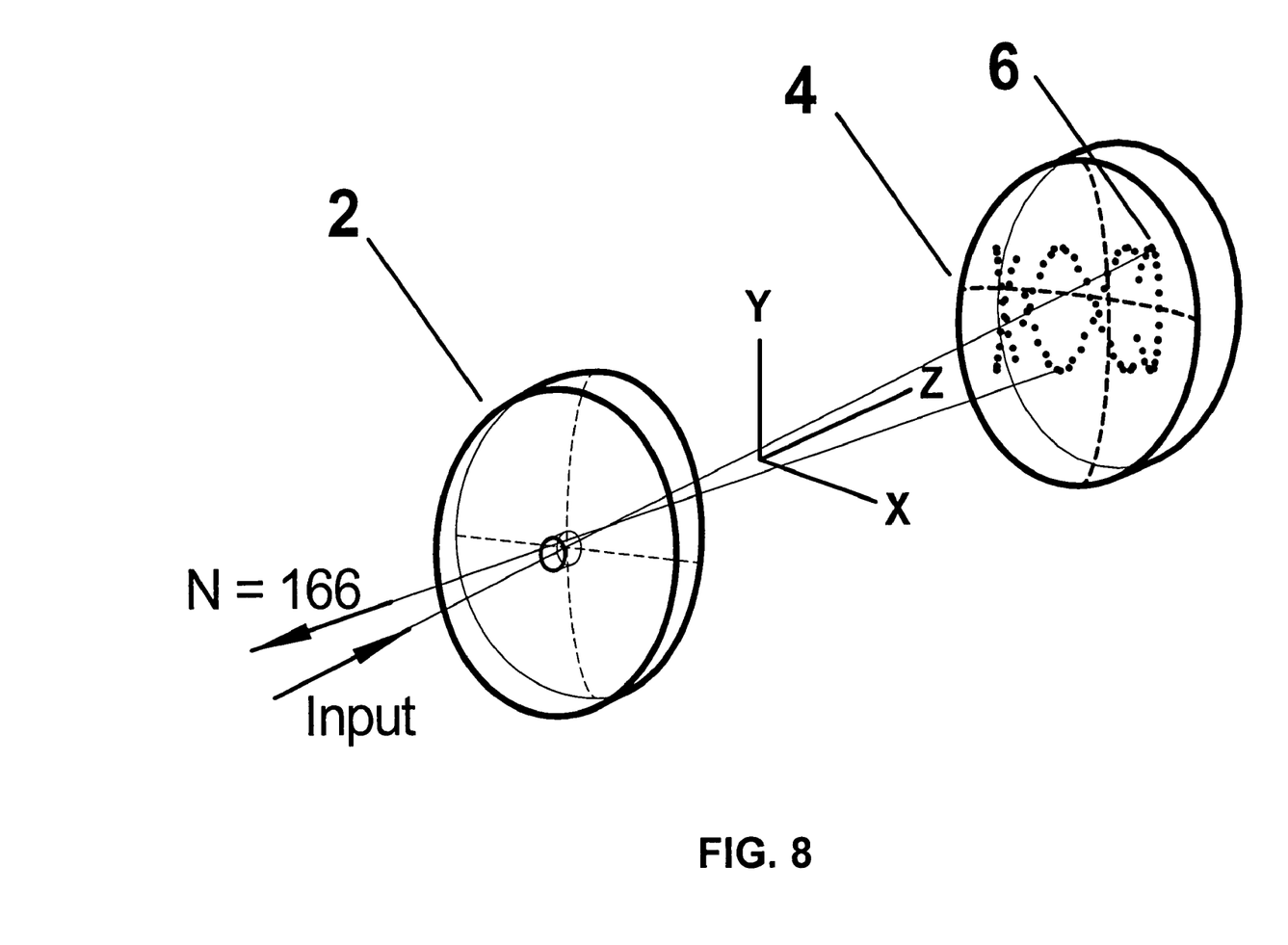
FIG. 8 is a drawing of the cylindrical-spherical mirror cell of the invention having a center on-axis input hole and set for a dense spot pattern of 166 passes.

Other dense patterns of spots are now achievable by varying the mirror separation. For example, FIG. 8 illustrates a pattern for N=166 passes when the separation d=98.1 mm. In this case the output beam well is separated from the input beam and provides an excellent example for a usable dense pattern multipass cell.

Using other separations and input slopes, many different near re-entrant patterns can be readily found. Using a diode laser or other laser, tuned to a wavelength corresponding to an absorption feature of a selected gas, this cell could be used to measure the concentration of that absorbing gas. For example, a 760 nm laser could be used to monitor the concentration of molecular oxygen in this cell.

Unlike other dense pattern cells, where achieving alignment of spot patterns rely on the absolute manufactured focal lengths or relative twisting of the mirror axes, this system uses only the ratio d/f and the input slopes to select the number of passes.

Neither the input hole diameter, slope or mirror separations are restricted, except by stability constraints and by physical dimensions to be sure that all spots hit a mirrored surface. However, the better choices are to keep d approximately between 0.5 and 1.5 times the mean focal length, and the input hole diameter below 10% of the mirror diameters.

Note that the following variations may be employed:

(1) Different focal lengths on each mirror change patterns, spot sizes, stability criteria, but do not change overall usefulness.

(2) Using other input slopes changes the overall shape of the spot pattern, so that the exit patterns will change as predicted by the theory as spot trajectories cross the hole on earlier or later numbers of passes.

(3) Non-central input holes can also be used to allow similar patterns.

(4) Separate input and output holes—an additional output hole can be used to pick off pass N if properly positioned.

(5) The use of a prism, mirror or other compact optical device to couple the light into or out of the cell instead of a hole. Any such entrance and/or exit mechanism can be employed.

(6) Any stable cavity distance as restricted only by Eqn. 12 is allowed and possible, although solutions in range $0.5 \leq d/f \leq 1.5$ are most useful based on relative pattern diameter and useful total path lengths.

(7) Input beam focus is generally collimated or focused to some point into cell. It is often desirable to focus at midpoint of mirror separation so that all spots have approximately same diameter.

(8) Cell may be enclosed in sealed container to sample externally introduced gases or be open to the air for ambient sampling.

(9) Either mirror can be used with the input hole; the matrix formulas and analyses just have to revised accordingly. Exit patterns are similar in both cases.

Industrial Applicability

The invention is further illustrated by the following non-limiting examples.

EXAMPLE 1

The same cylindrical mirror cell as above except that the input hole is near the edge of the mirror.

EXAMPLE 2

A cylindrical-spherical mirror cell where the beam does not exit through the hole until after very many passes and is not detected after exiting. This may be very useful for cavity ringdown or photoacoustic absorption experiments where very long paths are desired and the exiting laser beam does not need to be directly detected.

EXAMPLE 3

A cylindrical-spherical mirror cell where the input hole is located in the spherical mirror and the cylindrical mirror has spots corresponding to odd-numbered passes.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A multiple pass optical cell comprising a pair of opposed mirrors, one spherical cylindrical and one spherical, an entrance mechanism for introducing light into the cell, and an exit mechanism for extracting light from the cell, wherein said entrance mechanism and exit mechanism are coextensive or non-coextensive.

2. The optical cell of claim 1 additionally comprising a rotation mount for at least said spherical cylindrical mirror permitting rotation with respect to a long axis of said cell.

3. The optical cell of claim 2 additionally comprising a mirror separation adjuster.

4. The optical cell of claim 3 wherein a plurality of number of passes of light between the two mirrors exists for light entering said entrance mechanism and exiting said exit mechanism for any given combination of mirror separation distance and rotation position of said cylindrical mirror with respect to a long axis of said cell.

5. The optical cell of claim 1 additionally comprising a mirror separation adjuster.

6. The optical cell of claim 5 wherein a plurality of number of passes of light between the two mirrors exists for light entering said entrance mechanism and exiting said exit mechanism for any mirror separation distance.

7. The optical cell of claim 5 wherein manufacturing tolerances as to mirror focal lengths are adjusted for by varying mirror separation distance.

8. A multiple pass optical cell comprising a pair of opposed mirrors, one spherical cylindrical and one spherical, an entrance mechanism for introducing light into the cell, and an exit mechanism for extracting light from the cell, wherein said entrance mechanism and exit mechanism are coextensive or non-coextensive, and wherein a plurality of number of passes of light between the two mirrors exists for light entering said entrance mechanism and exiting said exit mechanism, but wherein a pattern of spots on said mirrors established by said plurality of passes of light is non-reentrant.

9. The optical cell of claim 8 additionally comprising a rotation mount for at least said spherical cylindrical mirror permitting rotation with respect to a long axis of said cell.

10. The optical cell of claim 9 additionally comprising a mirror separation adjuster.

11. The optical cell of claim 10 wherein a plurality of number of passes of light between the two mirrors exists for light entering said entrance mechanism and exiting said exit mechanism for any given combination of mirror separation distance and rotation position of said cylindrical mirror with respect to a long axis of said cell.

12. The optical cell of claim 8 additionally comprising a mirror separation adjuster.

13. The optical cell of claim 12 wherein a plurality of number of passes of light between the two mirrors exists for light entering said entrance mechanism and exiting said exit mechanism for any mirror separation distance.

14. The optical cell of claim 12 wherein manufacturing tolerances as to mirror focal lengths are adjusted for by varying mirror separation distance.

15. A multiple pass optical cell method comprising the steps of:
providing a pair of opposed mirrors, one spherical cylindrical and one spherical;
introducing light into the cell via an entrance mechanism; and
extracting light from the cell via an exit mechanism; and
wherein the entrance mechanism and exit mechanism are coextensive or non-coextensive.

16. The method of claim 15 additionally comprising the step of rotating at least the spherical cylindrical mirror with respect to a long axis of said cell.

17. The method of claim 16 additionally comprising adjusting mirror separation.

18. The method of claim 17 wherein a plurality of number of passes of light between the two mirrors exists for light entering the entrance mechanism and exiting the exit mechanism for any given combination of mirror separation distance and rotation position of the cylindrical mirror with respect to a long axis of said cell.

19. The method of claim 15 additionally comprising adjusting mirror separation.

20. The method of claim 19 wherein a plurality of number of passes of light between the two mirrors exists for light entering the entrance mechanism and exiting the exit mechanism for any mirror separation distance.

21. The method of claim 19 wherein manufacturing tolerances as to mirror focal lengths are adjusted for by varying mirror separation distance.

22. The method of claim 15 additionally comprising the step of initially aligning the mirrors using a fully reentrant test condition.

23. A multiple pass optical cell method comprising the steps of:
providing a pair of opposed mirrors, one spherical cylindrical and one spherical;
introducing light into the cell via an entrance mechanism; and
extracting light from the cell via an exit mechanism; and
wherein the entrance mechanism and exit mechanism are coextensive or non-coextensive; and
wherein a plurality of number of passes of light between the two mirrors exists for light entering the entrance mechanism and exiting the exit mechanism, but wherein a pattern of spots on the mirrors established by the plurality of passes of light is non-reentrant.

24. The method of claim 23 additionally rotating at least said spherical cylindrical mirror with respect to a long axis of the cell.

25. The method of claim 24 additionally comprising adjusting mirror separation.

26. The method of claim 25 wherein a plurality of number of passes of light between the two mirrors exists for light entering the entrance mechanism and exiting the exit mechanism for any given combination of mirror separation distance and rotation position of the cylindrical mirror with respect to a long axis of said cell.

27. The method of claim 23 additionally comprising adjusting mirror separation.

28. The method of claim 27 wherein a plurality of number of passes of light between the two mirrors exists for light entering the entrance mechanism and exiting the exit mechanism for any mirror separation distance.

29. The method of claim 27 wherein manufacturing tolerances as to mirror focal lengths are adjusted for by varying mirror separation distance.

30. The method of claim 23 additionally comprising the step of initially aligning the mirrors using a fully reentrant test condition.

31. A method of aligning a multiple pass optical cell comprising a pair of opposed mirrors, one spherical cylindrical and one spherical, the method comprising the steps of:
introducing light into the cell via an entrance mechanism and extracting light from the cell via an exit mechanism, wherein the entrance mechanism and exit mechanism are coextensive or non-coextensive;
aligning the mirrors using a fully reentrant test condition; and
subsequently adjusting the mirrors such that a plurality of number of passes of light between the two mirrors exists for light entering a cell entrance mechanism and exiting a cell exit mechanism, but wherein a pattern of spots on the mirrors established by the plurality of passes of light is non-reentrant.

* * * * *